US008834845B2

(12) United States Patent
Nies et al.

(10) Patent No.: US 8,834,845 B2
(45) Date of Patent: Sep. 16, 2014

(54) BIOACTIVE BONE CEMENT AND METHOD FOR ITS PRODUCTION

(75) Inventors: Berthold Nies, Fränkisch-Crumbach (DE); Werner Siol, Darmstadt (DE)

(73) Assignee: InnoTERE GmbH, Radebeul (DE)

( * ) Notice: Subject to any disclaimer, the term of this patent is extended or adjusted under 35 U.S.C. 154(b) by 475 days.

(21) Appl. No.: 12/750,782

(22) Filed: Mar. 31, 2010

(65) Prior Publication Data

US 2010/0272649 A1    Oct. 28, 2010

(30) Foreign Application Priority Data

Apr. 2, 2009    (DE) .......................... 10 2009 017 258

(51) Int. Cl.
    *A61F 2/02*    (2006.01)
    *A61L 24/06*    (2006.01)

(52) U.S. Cl.
    CPC .............. *A61L 24/06* (2013.01); *Y10S 977/904* (2013.01); *Y10S 977/908* (2013.01)
    USPC ............ 424/9.4; 523/113; 523/116; 424/423; 424/501; 977/904; 977/908; 623/23.62

(58) Field of Classification Search
    CPC ......... A61L 27/16; A61L 27/48; A61L 27/54; A61K 9/5138
    USPC ................... 523/116, 113; 424/9.4, 423, 501; 977/904, 908; 623/23.62
    See application file for complete search history.

(56) References Cited

U.S. PATENT DOCUMENTS

| 4,268,639 | A | * | 5/1981 | Seidel et al. ................... 525/303 |
| 4,535,485 | A | * | 8/1985 | Ashman et al. ............ 623/23.72 |
| 4,617,327 | A | * | 10/1986 | Podszun ....................... 523/116 |
| 5,264,215 | A |   | 11/1993 | Nakabayashi et al. |
| 6,300,390 | B1 |   | 10/2001 | Angeletakis |
| 2004/0132859 | A1 | * | 7/2004 | Puckett, Jr. et al. ........... 523/118 |
| 2007/0238808 | A1 | * | 10/2007 | Goldberg et al. ............. 523/116 |
| 2008/0194729 | A1 |   | 8/2008 | Nies |
| 2008/0200482 | A1 |   | 8/2008 | Petereit et al. |
| 2009/0239970 | A1 | * | 9/2009 | Rodrigues et al. ............ 523/117 |
| 2011/0054392 | A1 |   | 3/2011 | Nies |

FOREIGN PATENT DOCUMENTS

WO    2006/122678 A2    11/2006
WO    2008/116905 A2    10/2008

OTHER PUBLICATIONS

Miyazaki et al.: Bioactive PMMA bone cement prepared by modification with methacryloxypropyltrimethoxysilane and calcium chloride; J. Biomed. Mater. Res. 2003, 67A(4), pp. 1417-1423.

* cited by examiner

*Primary Examiner* — Michael Pepitone
(74) *Attorney, Agent, or Firm* — Gudrun E. Huckett

(57) ABSTRACT

A bioactive PMMA (polymethylmethacrylate) bone cement contains a powder component and a reactive monomer liquid, wherein the powder component and the reactive monomer liquid when mixed with one another react with one another and form a polymer-based solid material. The powder component contains particulate polymer powder of polymethylmethacrylates; a radical starter; and anionic copolymer nanoparticles. The anionic copolymer nanoparticles are distributed in nano-particulate form within the particulate powder component or coated as a film on particles of the particulate polymer powder.

14 Claims, 7 Drawing Sheets a)

LV51_A_Ref_48h, 11.07.08, 1kV, 7mm, 5000x    4μm b)

LV51_C_ 48h, 11.07.08, 1kV, 7mm, 5000x    5μm

REF a) 48h

LV52_S_Ref_ 48h, 11.07.08, 1kV, 7mm, 5000x b) 7d

LV52_S_Ref_ 7d, 11.07.08, 1kV, 6mm, 5000x

MAA, $Na_2CO_3$, $CaCl_2$ c) 48h

S6 _ 48h, 11.07.08, 1kV, 7mm, 5000x d) 7d

S6 _ 7d, 11.07.08, 1kV, 6mm, 5000x a)

b)

BIOACTIVE BONE CEMENT AND METHOD FOR ITS PRODUCTION

BACKGROUND OF THE INVENTION

The invention concerns improved bioactive PMMA bone cements that consist of a powder component and a reactive organic liquid that, when mixed, react with one another and form a polymer-based solid material.

PMMA bone cements are clinically used primarily for attachment of joint implants. For about 50 years, they have been established in clinical practice and today are used annually in approximately 5 million cases worldwide. The chemical composition of the bone cements has practically remained unchanged throughout this time.

A deficit of bone cements that are available currently is their lack of bonding to the bone. Bone cements according to the prior art after implantation are encapsulated by a thin connective tissue layer that is the result of a mild foreign body reaction. This connective tissue layer impairs the direct force transmission between implant and bone and in the end can lead to a premature loosening of the prosthesis.

In order to improve the direct bonding of bone cement to the bone, already various approaches have been followed in the past. The goal of these approaches resides in offering calcium phosphate surfaces to the bone. Such calcium phosphate layers (in particular hydroxyl apatite) have a similar composition as natural bone material and promote therefore binding of bone cells to the bone cement. These bone cells produce then new bone substance and promote in this way intergrowth of bone cement and bone. This effect is referred to also herein (and in the scientific literature) as bioactivity of bone cement.

The approaches for providing bioactive bone cements are based currently either on the addition of bioactive substances to the bone cement, wherein some of the admixed substances may become effective on the cement surface. An alternative to this resides in producing bioactive layers on the cement surface that after implantation may be formed as deposits from the surrounding body fluid or from released substances of the bone cement. The formation of calcium phosphate layers on the surface of the cured bone cement in (simulated) body fluid or after implantation is also referred to herein as mineralization.

Known bone cements that cause mineralization of the cement surface are disclosed in Miyazaki et al. (Bioactive PMMA bone cement prepared by modification with methacryloxypropyltrimethoxysilane and calcium chloride; J. Biomed. Mater. Res. 2003, 67A(4) 1417-1423). In this connection, MPS (methacryloxypropyl trimethoxysilane) and $CaCl_2$ are added to PMMA bone cements. The mineralization of the cement surface is achieved only at very high concentrations of additives. For a reliable mineralization in simulated body fluid within 3 days a combination of 16% $CaCl_2$ and 20% MPS is required. Even addition of 50% MPS (without $CaCl_2$) cause no precipitation of calcium phosphates/apatites within 14 days. This means that without calcium salt addition no mineralization occurs at all. The quantitatively high additions for mineralization also cause a significant change (worsening) of the cement properties.

U.S. Pat. No. 5,264,215 B1 discloses bone cements to which are added monomers of 4-MET (4-methacryloxyethyl trimellitic acid) or 4-META (4-methacryloxyethyl trimellitic anhydride) in combination with calcium phosphates, in particular hydroxyl apatites. These cement formulation have the disadvantage that unreacted monomer additives may reach the body. The insoluble mineral additive of calcium phosphate does not promote the mineralization.

WO 2006/122678 A2 discloses bioactive PMMA bone cements that obtain their bioactivity as a result of use of at least one of the following additives: monomers with carboxyl, sulfate, phosphate or phosphonate groups as anionic groups and at least one polymerizable unit, co-oligomers or copolymers of these monomers (that are added to the monomer liquid), water-soluble calcium salts or biocompatible buffering substances. It is the object of the present invention to provide a bioactive bone cement that after implantation forms a bioactive surface and promotes the formation of calcium phosphate phases on the cement surface and during the curing reaction and after its implantation practically cannot release any unreacted anionic monomers.

A bone cement is to be provided that with respect to preparation, handling properties, and biologic/medical properties has significant advantages. In particular, a long shelf life is to be ensured. Moreover, the use of a wider palette of anionic monomers is to be enabled. The bone cement should enable adjustment of the cement properties in a targeted fashion. Toxic effects that result from unpolymerized added monomers are to be prevented. A higher availability and effectivity of mineralization seeds on the cement surface are to be enabled. The bone cement should be compatible with all other requirements with respect to orthopedic bone cements and with all typical cement components so that the user can employ the bioactive bone cement in the same way as a conventional bone cement. Mineral components for the purpose of obtaining a bioactive cement surface should be eliminated as much as possible or completely.

SUMMARY OF THE INVENTION

The object is solved by a bioactive PMMA bone cement, comprising a powder component and a reactive monomer liquid that upon mixing react with one another and form a polymer-based solid material, wherein the powder component contains particulate polymer powder of polymethylmethacrylates and a radical starter. The bioactive PMMA bone cement is characterized in that the powder component contains anionic copolymer nanoparticles or in that the particles of the polymer powder of the powder component are coated with a film of anionic copolymers.

In this context, the term "bone cements" is to be understood exclusively as meaning PMMA bone cements. PMMA bone cements are generally known cements that cure exclusively by radical polymerization. They are comprised of a powder component and a reactive liquid (referred to herein also as reactive monomer liquid or monomer liquid). In this connection, the powder component contains one or several powdery and thus particulate polymers (also referred to herein as polymer powder). The polymer powders are comprised of acrylates, methacrylates or styrene. In this connection, the polymers are either present as homopolymers or their mixtures or as copolymers with participation of the aforementioned monomers or as mixtures of such copolymers or as mixtures of homopolymers and copolymers. The aforementioned polymers are referred to for reasons of simplification as polymethylmethacrylates (PMMA) (therefore also the commonly employed term "PMMA bone cements" in the literature). The powder component of the PMMA bone cements contain furthermore a radical starter as well as optionally x-ray contrast agents. As x-ray contrast agents preferably barium sulfate or zirconium dioxide are used. The proportion of x-ray contrast agent in the powder component of the PMMA cement is maximally 50% by weight, preferably maximally 10% by weight. Radical starters are known in the art. Preferably, dibenzoyl peroxide (BPO) is used as a radical starter.

The polymer powders are comprised in general completely or predominantly of so-called bead polymer obtained by suspension polymerization that have particle diameters of approximately 10-100 µm. The particle diameter of the x-ray contrast agents optionally contained in the powder component is usually in the range of 0.5-30 µm.

Expressly excluded are other cements, known under the term "bone cements", that do not exclusively cure by radical polymerization. Excluded particularly are so-called glass ionomer cements that are usually employed in the dental field.

The polymer powder and optionally the x-ray contrast agents do not participate in the actual polymerization reaction that leads to cement curing. They serve, on the one hand, as a filler in order to reduce the quantity of reactive monomer and thus the shrinkage going hand in hand with polymerization and heat development. On the other hand, they serve, depending on the solubility in the monomer, for adjusting the mechanical properties and the handling properties.

The reactive organic liquid contains primarily monomeric methylmethacrylate (MMA) or other esters of acrylic acid or methacrylic acid or combinations thereof. Furthermore, the reactive liquid contains a co-starter (also referred to as activator or co-initiator) and a stabilizer or inhibitor. Preferred co-starters are dimethyl-p-toluidine (DMPT) or other tertiary amines that are used in almost all commercial bone cements. As inhibitors preferably hydroquinone and one of its derivatives are used.

Optionally, the PMMA bone cements contain further substances, such as preferably active ingredients, in particular antibiotics, or coloring agents. Further substances may be contained in the powder component as well as in the reactive liquid or in both components. Optionally, active ingredients are not added until immediately before or during mixing of the bone cement.

The PMMA bone cement according to the invention is comprised of a powder to component and a reactive organic liquid, wherein the powder component of the bone cement contains, aside from the polymer powder, anionic co-oligomers or anionic copolymers. In this connection, the latter are present in nano-particulate form. In this context, nanoparticles of anionic co-oligomers as well as nanoparticles of anionic copolymers are referred to in a simplified fashion as "anionic copolymer nanoparticles". Anionic co-oligomers or copolymers contain free anionic groups or anionic groups that can dissociate or hydrolyze when in contact with aqueous solutions. Optionally, the anionic copolymer nanoparticles are deposited on the significantly larger bead polymers of the polymer powder and form in this way a layer on the particles of the polymer powder. This is referred to herein also as a nano-particulate coating of anionic copolymer nanoparticles.

According to the invention, the anionic co-oligomers or copolymers are present in the powder component as nanoparticles with a size of 30 to 5,000 nm, preferred of 30 to 1,000 nm. Alternatively, the anionic copolymer nanoparticles are present as a nano-particulate coating on the polymeric powder components of the powder component.

As an alternative to the use of nano-particulate co-oligomers or copolymers with anionic groups, they are present as thin layers (film) on the particles of the polymer powder of the bone cement. The thickness of the film is in this connection within the size range of the diameter of the anionic copolymer nanoparticles. In the embodiment as a film of co-oligomers or copolymers with anionic groups (referred to summarily as anionic copolymers) they are not present in nano-particulate form but form a thin layer on the bead polymers of the polymer powder. This can be achieved preferably in that first a nano-particulate coating of anionic copolymer nanoparticles is applied from aqueous emulsion wherein the water is removed above the minimum film-forming temperature (MFT) or the coated powder is incubated above the MFT. Alternatively, films of anionic copolymers can be prepared in a known process from solutions of the anionic copolymers in highly volatile solvents in that the polymer powder is mixed with the solution and the solvent is removed.

The anionic copolymer nanoparticles contained in the bone cement according to the invention are preferably prepared by emulsion polymerization.

Anionic copolymers or anionic copolymer nanoparticles contain preferably a molar proportion of 0.01% to 25% of anionic monomer units (anionic co-monomers). A contents that surpasses significantly 25% leads to incompatibility with the PMMA matrix and to solubility in aqueous medium.

The powder component of the bioactive PMMA bone cement according to the invention contains preferably 0.1% to 50% by weight, especially preferred 1 to 30% by weight, of the anionic copolymer or anionic copolymer nanoparticles.

The anionic copolymers or co-oligomers contain anionic monomer units of the same kind or different kind, in particular monomer units that contain phosphate groups and/or carboxyl groups. Moreover, in the powder component different anionic copolymers or anionic copolymer nanoparticles may be contained that each have different functional anionic groups. Preferably, a part of the anionic copolymers or anionic copolymer nanoparticles contain only a minimal quantity of anionic monomers.

Preferably, the powder component of the PMMA bone cement according to the invention contains additionally copolymer nanoparticles that do not contain anionic monomer units (referred to herein also as non-anionic copolymer nanoparticles). These non-anionic copolymer nanoparticles in this case are preferably present in combination with anionic copolymer nanoparticles.

The bone cement according to the invention has the advantage that, by selection of the anionic monomer units and/or the combination of different anionic monomer units in the anionic copolymers, the contents of anionic monomer units in the anionic copolymers as well as the proportion of non-anionic copolymer nanoparticles or films of anionic copolymers, the cement properties as well as the bioactive properties of the PMMA bone cement can be influenced in a targeted fashion.

Preferred in these combinations are mixtures of non-anionic copolymer nanoparticles and anionic copolymer nanoparticles. Preferably, mixtures of different anionic copolymer nanoparticles are used herein. Especially preferred are mixtures of anionic copolymer nanoparticles with phosphate group-containing co-monomers (without carboxyl group-containing co-monomers), anionic copolymer nanoparticles with carboxyl group-containing co-monomers (without phosphate group-containing co-monomers) and anionic copolymer nanoparticles with phosphate group containing and carboxyl group-containing co-monomers.

At least one part of the anionic copolymers is not crosslinked and is therefore present as linear copolymers. The molecular weight of at least 50% of the anionic copolymers is 10,000-5,000,000 Dalton; preferred are anionic copolymers with a molecular weight of 20,000-800,000 Dalton wherein the range of 30,000-300,000 Dalton is especially preferred.

Anionic co-oligomers are molecules that are comprised of up to 50 units of anionic monomers and acrylate, methacrylate, styrene, vinyl monomers or monomers with ethylenically unsaturated double bond. Anionic copolymers are molecules of comparable build of more than 50 units of anionic monomers and acrylate, methacrylate, styrene, vinyl monomers or monomers with ethylenically unsaturated double bond and have a higher molecular weight than anionic co-oligomers.

The anionic co-oligomers and copolymers contain free anionic groups or anionic groups that can dissociate or hydrolyze when in contact with aqueous solutions. They are comprised of co-oligomers or copolymers of acrylate, methacrylate, styrene, vinyl monomers or monomers with ethylenically unsaturated double bond and of monomers with free, dissociatable or hydrolyzable anionic groups, wherein the anionic groups are carboxylic, phosphate, phosphonate or sulfate groups.

Preferred anionic monomers are methacrylic acid (MAA), 4-META, 4-MET, MAC10 (11-methacryloxy-1,1-undecane dicarboxylic acid), maleic acid, maleic acid anhydride, itaconic acid, itaconic acid anhydride, acrylamido glycolic acid, ethylene glycol-methacrylate phosphate or its homologs with more than one ethylene glycol unit, ethylene glycol-methacrylate phosphonate or its homologs with more than one ethylene glycol unit, sulfopropyl methacrylate or 2-acrylamido-2-methylpropane sulfonic acid.

Anionic copolymer nanoparticles contain preferably the following non-anionic monomer units: MMA, styrene, and/or further uncharged co-monomers that are conventionally used in bone cement, in particular methacrylate (MA) or butyl methacrylate. The total contents of anionic co-monomers relative to the total monomers is preferably 0.01 to 25%.

Further anionic monomers that are preferably components of anionic copolymer nanoparticles are disclosed in U.S. Pat. No. 6,300,390 B1. Herein a building block synthesis for anionic monomers is disclosed that have the property that they can be copolymerized with MMA. In this way, libraries of anionic monomers can be generated that have in common that they contain one or several anionic groups or groups that dissociate or hydrolyze to form them and at least one ethylenically unsaturated double bond by means of which they can copolymerize with acrylate, methacrylate, styrene, vinyl monomers or other monomers with ethylenically unsaturated double bond. The substances of these libraries differ only in regard to the composition of the spacers between both functionalities. When the thus obtained monomers are copolymerized, for example, with MMA by way of emulsion polymerization, new copolymers are produced that can be obtain in nanoparticulate form and can be used in the bone cements according to the invention.

Optionally, the copolymer nanoparticles are present as nano-particulate coatings on the polymer powder. The larger particles of the bone cement powder are coated with the smaller copolymer nanoparticles. In this connection, coating of the polymer powder is preferably done with a suspension of copolymer nanoparticles.

Optionally, nano-particulate coatings of several layers of copolymer nanoparticles are present on the particles of the polymer powder of the PMMA bone cement according to the present invention. This is dependent on the quantity of the added copolymer nanoparticles. Optionally, a proportion of the copolymer nanoparticles is present as a coating on the particles of the polymer powder and a further proportion is present as finely divided powdery copolymer nanoparticles.

Upon mixing of the powder component of the PMMA bone cement according to the invention with the reactive monomer liquid a high presence of anionic copolymers on the cement surface is advantageously present. The anionic copolymer nanoparticles cannot penetrate upon swelling of the polymer powder into the particles of the polymer powder. In this way, the anionic groups are available to a higher proportion on the cement surface as compared to, for example, the use of monomeric HEMA phosphate. The anionic copolymer nanoparticles or the films of anionic copolymers are therefore more effective seeds for the mineralization of the cement surface as compared to the use of anionic monomers or non-nano-particulate anionic co-oligomers or copolymers.

The PMMA bone cement according to the invention is comprised of a powder component and a reactive component. The powder component contains polymer powder that in a known way is selected from homopolymers or copolymers of acrylic acid esters, methacrylic acid esters, styrene, vinyl derivatives or their mixtures. The reactive liquid contains reactive organic monomers selected from methylmethacrylate, homolog esters of methacrylic acid or their mixtures.

According to a preferred embodiment of the invention, the powder component of the PMMA bone cement according to the invention is designed as a storage-stable paste. In this connection, the powder component contains at least one biocompatible polymer powder, anionic copolymer nanoparticles or films of anionic copolymers on the particles of the polymer powder, a starter component for initiating a polymerization reaction (radical starter), and a carrier liquid that serves for producing the paste. The carrier liquid is selected such that the polymer powder under normal conditions will not dissolve or significantly swell in the carrier liquid and that the starter component remains stable until mixing with the reactive liquid of the PMMA bone cement. The powder component contains in this connection, as described above, anionic copolymer nanoparticles that optionally are present as thin nano-particulate coatings on the particles of the polymer powder or films of anionic copolymers on the particles of the polymer powder. The powder component in the form of the storage-stable paste is mixed for initiating the curing reaction with a reactive monomer liquid wherein the latter is optionally also embodied as a paste. In this connection, the reactive monomer liquid contains a solution or a suspension of the reactive organic liquid with biocompatible polymers, in particular polyacrylmethacrylates.

Preferably, a portion of the anionic copolymer nanoparticles is added to the reactive monomer liquid. Preferably, the anionic copolymer nanoparticles are then dispersed or dissolved in the reactive liquid.

The preparation of the anionic copolymer nanoparticles contained in the bone cement according to the invention is realized preferably by emulsion polymerization. By means of this known method water-soluble co-monomers and hydrophobic, water-insoluble monomers can be copolymerized in a simple way. Typical for the method of emulsion polymerization is the formation of polymers in the form of an emulsion of very small particles that is referred to as latex. In general, the hydrophilic anionic monomer building blocks at the latex surface contribute to stabilization of the dispersion. A person skilled in the art of emulsion polymerization is well aware of the possibilities of preparation and targeted control of compositions of anionic and non-anionic copolymer nanoparticles.

Anionic copolymers of methylmethacrylate and dicarboxylic acids such as itaconic acid, maleic acid, fumaric acid or their anhydrides are preferably produced by emulsion polymerization in the way known in the art. In this connection, preferably the emulsion method or monomer fed-batch method is employed wherein a portion of the water as well as the total quantity or proportions of the initiator and of the emulsifying agent are initially placed into the reactor. The particle size according to this method can be controlled advantageously by the quantity of the initially placed emulsifying agent (compare DE 31 39 090).

Typical sizes of the individual polymer particles produced by the method of emulsion polymerization are in the range of a few nanometers up to a few micrometers. The diameter of the copolymer nanoparticles (anionic as well as non-anionic) used in the bone cement according to the invention is 30-5,000 nm, preferably 30-1,000 nm.

Preferred anionic copolymer nanoparticles are designed as particles with a core/shell configuration that can be produced by emulsion polymerization. In this connection, about a hydrophobic core a shell is polymerized that is rich in anionic monomers. Such emulsions with core/shell particles have a diameter of 50-5,000 nm, preferred 100-2,000 nm, especially preferred 100 to 1,000 nm, and most preferred 100 to 500 nm.

In general, these emulsions with particles with core/shell configuration are realized according to the method of fed-batch polymerization. In this connection, an emulsion of monomers, emulsifying agent, initiator and water is metered under polymerization conditions into a stirred reactor. The polymerization is controlled such that the metered-in emulsion is possibly polymerized immediately so that polymerization is realized at a high conversion rate. A change in monomer composition also leads to a change in the polymer composition of the latex particle. In this way, the preparation of the emulsion polymers with core/shell configuration is possible (see in this connection Examples 1 and 2).

The emulsion polymerization according to the fed-batch method also provides the possibility to incorporate into the copolymer chains anionic monomers that, because of their bad copolymerization parameters, cannot be copolymerized with MMA under other conditions, or only with difficulty. Such monomers are, for example, maleic acid and acrylic acid. In general, for the preparation of copolymer nanoparticles the fed-batch emulsion method is preferred. Since the polar anionic monomers have the tendency to to destabilize the emulsion, a quick metering action of the emulsion after preparation is required. Optionally, the emulsion must be produced and added in several batches. Inasmuch as required, polymerization control agents, for example, mercaptanes, can be used for limiting the molecular weight.

On the other hand, as mentioned above, it is advantageous when not all polymer chains have the same composition. Preferably, the molar proportion of anionic monomers with respect to the total copolymer is 0.01-25%.

Especially preferred are anionic copolymer nanoparticles in which blocks of non-polar monomer units or blocks of non-polar monomer units with a minimal contents of anionic monomer units are covalently bonded to polymer sequences that are rich in anionic monomer units. Such copolymer nanoparticles are obtained preferably by graft copolymerization.

Methods of obtaining nano-particulate polymer powders from the emulsions are known to a person skilled in the art. Preferred is the direct coating of the polymer powder of the powder component of the bone cement with an emulsion of copolymer nanoparticles and subsequent drying. In this way, nano-particulate coatings of copolymer nanoparticles are formed on the particles of the polymer powder.

A further preferred method for obtaining the solid copolymer nanoparticles from the emulsion is by drying, in particular spray-drying or freeze-drying, by precipitation of multivalent ions or by freeze coagulation. Precipitation or freeze coagulation have the advantage that the solid material of copolymer nanoparticles can be washed and therefore optionally still contained emulsifying agent residues or residual monomers can be removed. Preferably, the residual contents of unpolymerized anionic monomers relative to the solid material of the copolymer nanoparticles is <1% by weight, preferably <0.1% by weight, and particularly preferred <100 ppm. Accordingly, in the bone cement according to the invention significantly reduced quantities of anionic monomers are present as compared to what is achievable when using anionic monomers or non-nano-particulate anionic co-oligomers or copolymers.

In contrast to the copolymer nanoparticles used in the bone cement according to the invention the polymer powders contained in the powder component and comprised of polymethylmethacrylates are usually produced by suspension polymerization (bead polymerization). The average diameter of the particles of the polymer powder is approximately 10-100 µm. The diameter of the copolymer nanoparticles is thus approximately 10-1,000 times smaller than the diameter of the particles of the polymer powder. The volume of the copolymer nanoparticles is smaller by a factor of $10^3$ to $10^9$ than the volume of the particles of the polymer powder.

In further embodiments of the invention, the bone cement according to the invention contains further additives that increase the mineralization tendency of the cement surface after implantation.

Preferably, the bone cement according to the invention contains water-soluble, bio-compatible calcium salts in the powder component. Preferably, the solubility of the calcium salts in water is greater than 1 g/l. In particular, $CaCl_2$, $Ca(NO_3)_2$, calcium acetate, calcium ascorbate, another calcium salt of an organic acid that naturally occurs in the animal organism or a mixture of the aforementioned salts are used. In this connection, the calcium salts are used in a proportion of 0.01 to 20% by weight, preferably between 0.1 and 10% by weight relative to the total mass of the bone cement.

The addition of water-soluble calcium salts serves for increasing the mineralization tendency of the bone cement surface. The release of $Ca^{2+}$ ions from the surface-near cement matrix increases locally the $Ca^{2+}$ concentration in the vicinity of the cement and leads to a faster and stronger formation of calcium phosphate phases at the crystallization seeds and accelerates in this way the mineralization of the cement surface.

Preferably, the bone cement according to the invention contains in the powder component bio-compatible buffering substances whose greatest buffering capacity is within the neutral or slightly basic range, preferably, buffering substances whose pK value is at least 7.4. Especially preferred buffering substances are $Na_2CO_3$, $NaHCO_3$, $Na_3PO_4$, $Na_2HPO_4$, $Na_3$-citrate, $K_2CO_3$, $KHCO_3$, $K_3PO_4$, $K_2HPO_4$, $K_3$-citrate. The buffering substances are used in a proportion of 0.1 to 15% by weight, preferably 0.1 to 10% by weight, especially preferred between 0.1 and 7.5% by weight relative to the total mass of the cement.

The addition of the biocompatible buffering substances serves also for increasing the mineralization tendency of the bone cement surface. By release of the buffering substances at the cement surface a local increase of the pH value at the cement surface is effected. Since the solubility and crystallization of calcium phosphate phases depends on the pH-value, the local increase of the pH value leads to an increased deposition of calcium phosphate phases, in particular of hydroxyl apatite.

Especially preferred in the bone cements according to the invention are water-soluble calcium salts and bio-compatible buffering substances. They are preferably admixed to the powder component. Optionally, the bone cement according to the invention contains x-ray contrast agents, antibiotics, other antimicrobial agents, and/or anti-inflammatory agents that are capable of suppressing inflammation reactions of the body after implantation of the cement. They are contained preferably in the powder component.

Bone cements according to the invention in further embodiments of the invention are formulated in dosed or partially dosed mixing systems and/or are present as ready-made systems in sterilized form. In this connection, the powder component and reactive monomer liquid are provided in spatially separated packages and are admixed with one another not until immediately before use. In this connection, different mixing systems may be employed. Closed mixing systems are to be understood as those containers in which powder and liquid are already packaged within the mixing system and without opening one of the two components are mixed within the mixing systems and, out of the systems, directly applied into the bone. In partially dosed mixing systems the liquid is packaged separately while the powder is already contained in the mixing system.

In further embodiments of the invention, the bone cements according to the invention are present as kits wherein powder component and reactive monomer liquid are provided in separately packaged containers. In this connection, their quantity that is provided in the respective packaging is metered such that powder component and monomer liquid immediately before use can be combined and mixed with one another without further assessments of the quantities or volumes to be mixed (for example, by weighing) being required. Optionally, additives that are contained in a bone cement according to the invention within the powder component, in particular x-ray contrast agents, antibiotics, antimicrobial agents and/or anti-inflammatory agents, are packaged separately in the kit and are admixed before application first with the powder component and subsequently combined with the monomer liquid. The aforementioned additives are also provided in the kit in quantities that enable immediate admixture with the powder component (without further assessment of quantity or volume).

The invention comprises furthermore the use of the bone cement according to the invention for anchoring prosthesis components in the bone, for stiffening of bone, for filling and reconstructing bone defects of all kinds, as a dowel for bone screws or as an implant material for anchoring screws and other implants for osteosynthesis.

Bone cements according to the invention provide surprisingly the advantage of a particularly effective and expedient bioactivation and mineralization and therefore improved osteoconductivity.

The additions of the copolymer nanoparticles to the powder components have no effect on the stability of the reactive monomer liquids. Therefore, there are no limitations with respect to the shelf life of the monomers, which in case of bone cements is the limiting to component regarding shelf life. Therefore, the bone cements according to the invention overcome the disadvantages of those bone cements that contain anionic monomer additives that are added to the monomer liquid and therefore experience limitations with respect to their shelf life.

PMMA copolymers with anionic co-monomers are known per se and are considered physicochemically stable. This applies only to a limited extent to the corresponding monomers because the monomers have differently strong tendencies to undergo spontaneous polymerization. Since for anionic monomers and their mixtures with MMA no shelf life data are available, they would have to be determined for each monomer formulation in a complex way.

By providing anionic copolymers in the form of nanoparticles or as nano-particulate coatings or thin layers (films) on the polymer powder, they are dissolved quickly or at least begin to swell quickly when mixing the powder component of bone cement with the reactive liquid and are therefore quickly and effectively incorporated into the cement matrix.

The method of emulsion polymerization for producing the copolymer nanoparticles enables the targeted adjustment of molecular weight, level of copolymerization, and particle size. When using anionic monomers that are to be copolymerized with the reactive monomer liquid, only co-monomers can be used however that under the environmental conditions, i.e., the conditions of use of bone cements, have polymerization kinetics comparable to those of the reactive monomer liquid (MMA).

By using anionic copolymer nanoparticles or films of anionic copolymers, co-monomers can also be used that are not compatible with the reactive monomer liquid of the bone cement. Advantageously, anionic co-monomers can be used that do not dissolve in the reactive monomer liquid or have a significantly different polymerization rate. This can be regulated in the preparation of copolymer nanoparticles. However, when adding anionic monomers in situ polymerization takes place in which the aforementioned monomer properties are technologically and toxicologically disadvantageous.

Advantageously, anionic copolymer nanoparticles can be produced also by use of monomers that has no biological compatibility as a free monomer or whose biological compatibility is not documented because, in the form of copolymers, they do not come into contact with the tissue as a free substance. This applies, for example, to 4-MET or 4-META that are known from dental technology but up to now have not been used as a monomer additive in bone cements for the aforementioned reason. Accordingly, no long-term experiences with this monomer in implant materials exist. U.S. Pat. No. 5,264,215 discloses a bioactive bone cement wherein the reactive monomer liquid to 95% is MMA and to 5% is 4-META. The contents of 4-META as a residual monomer after curing is between 0.42% and 1.09%, depending on the cement formulation. The relative contents of 4-META residual monomers was 2-3 times higher than the relative residual monomer contents of MMA. This has the disadvantage that after implantation of the bone cement unreacted monomers of non-biocompatible 4-META may reach the body and that even after curing of the cement this monomer may escape from the cement into the body. This can be avoided by use of 4-META-containing anionic copolymer nanoparticles in a bone cement according to the invention.

Further special advantages of the use of anionic monomers as co-monomers in anionic copolymer nanoparticles or films of anionic copolymers instead of a direct use of anionic monomers as additive to bone cement is based on the solubility behavior of suitable anionic co-monomers. For example, the polar anionic monomers are often very well soluble in water; their solubility in organic media, in particular in the reactive monomer liquid (for example, MMA) is however minimal. In general, the solubility of the anionic monomers is even less when polymers (for example, PMMA) are contained in dissolved form in the reactive monomer liquid. Therefore, in case of a direct use of anionic monomers it is to be expected that the reactive monomer liquid will polymerize in the organic phase while polar anionic monomers primarily pass into the aqueous phase in the environment of the bone cement. This leads disadvantageously to the PMMA phase and the tissue phase not binding properly.

These disadvantages are overcome by the solution presented by the present invention according to which anionic copolymer nanoparticles or films of anionic copolymers in PMMA bone cements are used. For their preparation the anionic monomers and the non-polar monomers (in particular MMA) are copolymerized in a solvent that is suitable for both monomers and for both polymer chains (in particular esters or alcohols). In this way, homogenous solutions of copolymers are obtainable that within one polymer chain contain anionic as well as non-polar co-monomers. The thus designed copolymers with anionic and non-polar co-monomers will arrange themselves upon curing of the bone cement according to the invention in such a way that the sequences that are rich in non-polar co-monomers are oriented toward the polymethylmethacrylates while the regions rich in anionic co-monomers are concentrated on the bone cement surface.

When using anionic copolymer nanoparticles or films of anionic copolymers that contain biocompatible anionic monomer units, for example, hydroxyethyl methacrylate phosphate (HEMA phosphate or HEMA-P) in combination with non-polar co-monomers, for example, MMA, the bone cement according to the invention has advantages relative to the art-known addition of anionic monomers to reactive monomer liquids of the bone cement.

By using monomers, an in-situ polymerization takes place that does not lead to a complete conversion of the monomers to polymers. For the use of, for example, HEMA phosphate in bone cements no satisfactory data with regard to biocompatibility for the implantable use in bone cements exist. For this application, these data would have to be acquired in a complex way; this is not required in case of use of copolymer nanoparticles because it is ensured that they do not contain any free monomer units. For the copolymers themselves there is no bioavailability, i.e., they remain bonded within the cement matrix and are not released into the tissue.

A further disadvantage of prior methods is that anionic monomers usually are not available commercially as a pure substance of a quality that is required for use in bone cement monomers. The production of anionic monomers for this application contributes to a significant cost increase in bone cement preparation. For manufacturing anionic copolymer nanoparticles the commercially available quality of the anionic monomers is sufficient because the anionic copolymer nanoparticles per se can be produced in a way that leads to pure products. This is realized primarily by the method of emulsion polymerization. After polymerization the anionic copolymer nanoparticles can be freed of impurities by washing.

The use of anionic copolymer nanoparticles in the bone cement according to the invention eliminates prior limitations with regard to solubility and stability of the employable monomers. This will be explained with the aid of HEMA phosphate in an exemplary fashion. HEMA phosphate is dissolved homogeneously only in minimal concentrations in bone cement monomer and therefore was useable only with difficulty in prior art bone cement formulations. In copolymers substantially higher proportions can be achieved. In regard to the stability of HEMA phosphate in bone cement monomer no data are available. However, practically unlimited shelf life is to be expected when used as a co-monomer with MMA in a polymer.

The preparation of copolymers of HEMA phosphate and MMA by emulsion polymerization can be controlled exactly and leads to nano-particulate polymer powders. The co-monomer distribution in the polymer molecule can be affected in a target fashion so that the spacing of the anionic groups can be controlled. In this way, the effectiveness of the anionic groups as mineralization seeds can be influenced additionally. On the other hand, the effectiveness of HEMA phosphate that is added as a monomer to the monomer liquid can be substantially only influenced by its concentration. The use of the copolymer as nanoparticles ensures on the one hand the excellent distribution in the bone cement powder and on the other hand the excellent (fast) solubility or swelling capability as soon as the bone cement powder is mixed with the monomer liquid.

The approach and the solution according to the invention of the problem known in the prior art will be apparent from the following explanations, illustrations, and examples in more detail. The subsequent explanations, illustrations and examples will explain the invention in more detail without limiting the invention.

BRIEF DESCRIPTION OF THE DRAWINGS

Based on the following illustrations the examples of the invention will be explained. It is shown in.

DESCRIPTION OF PREFERRED EMBODIMENTS

Example 1

Figure 1:
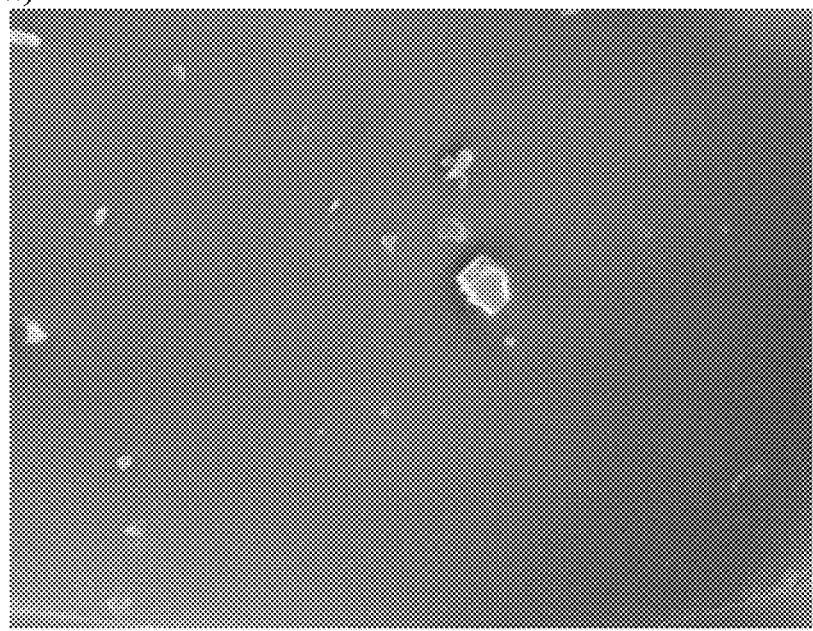
FIG. 1 REM images of cured bone cements with anionic copolymer nanoparticles (with HEMA-P as anionic monomer), $CaCl_2$ and $Na_2CO_3$ (b) and a reference bone cement without anionic copolymer nanoparticles, $CaCl_2$ and $Na_2CO_3$ (a) after 48 h incubation in simulated body fluid (SBF).
Figure 1:
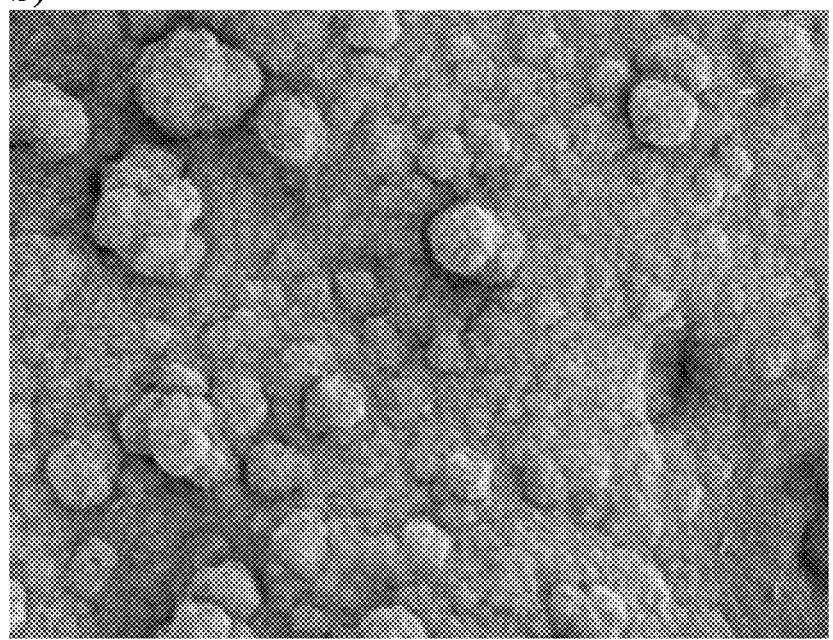

Preparation of Anionic Copolymer Nanoparticles with Core/Shell Configuration and Methacrylic Acid (MAA) as Anionic Co-Monomer By a method of emulsion polymerization anionic copolymer nanoparticles are produced that contain MAA as anionic co-monomer.

For this purpose, 0.5 g potassium peroxide disulfate and 10 g of an emulsifying agent solution (0.5 g sodium lauryl sulfate in 70 g of water) in 950 grams of water are placed into a stirred 2 l four-neck flask. Subsequently, at 80° C. under argon 60 g emulsifying agent solution were metered in. Parallel to this, the following monomers were metered in: first 226 g MMA; subsequently, a monomer mixture of 202.5 g MMA and 22.5 g methacrylic acid (MAA). The total time of the metering action was 3 hours. In this way, a stable dispersion with a solids content of 30% was obtained.

1 kg of the thus produced dispersion was frozen at −20° C., then thawed with hot water, filtered off by suction, washed and dried. 287 g of a fine powder of anionic copolymer nanoparticles was obtained. The particle diameter was approximately 300 nm.

Example 2

Preparation of Anionic Copolymer Nanoparticles with Core/Shell Configuration with Hydroxyethyl Methacrylate Phosphate (HEMA-P) as Anionic Co-Monomer In a method of emulsion polymerization anionic copolymer nanoparticles were produced that contain HEMA-P as anionic co-monomer.

For this purpose, 0.13 g of sodium lauryl sulfate and 1.0 g potassium peroxide sulfate in 975 g water were placed into an apparatus according to Example 1 and heated to 80° C.

To this, first an emulsion of 233 g MMA, 0.7 g sodium lauryl sulfate, and 182 g water was metered in. Directly afterwards, a further emulsion, comprised of 11.4 g HEMA-P, 14.7 g MMA, 0.5 g sodium lauryl sulfate and 199 g water, was metered in. After metering in the emulsions, the mixture was stirred further at 80° C. for 1 hour. Subsequently, cooling to room temperature and filtration were carried out.

A stable dispersion with a solids content of 25% was obtained. By freezing, thawing and washing in analogy to the Example 1, anionic copolymer nanoparticles in the form of a white powder were obtained. The particles had a diameter of approximately 300 nm.

Example 3

Preparation and Testing of Bioactivity and Compression Strength of Bone Cements According to the Invention with Anionic Copolymer Nanoparticles with HEMA-P as Anionic Co-Monomer A bone cement according to the invention has the following composition:
powder component: polymer powder (PMMA particles, Palacos R of Heraeus Medical), anionic copolymer nanoparticles with HEMA-P as anionic co-monomer (in analogy to Example 2), $CaCl_2$, $Na_2CO_3$;
reactive monomer liquid: MMA (Palacos R, with co-initiator and inhibitor).

For producing the bone cement anionic copolymer nanoparticles of the Example 2 were mixed into a commercially available bone cement powder (Palacos R of Heraeus Medical). Before the mixing process the nanoparticles were ground in order to break up agglomerates. Alternatively, a nanoparticle suspension can be mixed with the bone cement powder and subsequently dried so that nano-particulate coatings of the anionic copolymer nanoparticles on the bone cement powder are obtainable.

The further additives $CaCl_2$ and $Na_2CO_3$ were first mechanically comminuted in a ball mill and subsequently admixed to the premixed nanoparticle bone cement powder. In order to ensure homogeneous distribution of the components, the modified cement powder was mixed in a drum on a roller.

The following table shows the composition of the individual solid additives to the powder component of the bone cement according to the invention in weight % (middle column) as well as the contents of anionic monomers HEMA-P in the cured bone cement.

| additive | proportion of additive [% by weight] | final contents of HEMA-P in the bone cement |
|---|---|---|
| HEMA-P copolymer nanoparticles | 20% | 0.5% HEMA-P |
| $Na_2CO_3$ | 5% | |
| $CaCl_2$ | 5% | |
| bone cement powder Palacos R | 70% | |

Subsequently, the bone cement powder was mixed with monomer liquid in a ratio of 2:1 (weight of powder/volume of monomer). As a monomer MMA was used. A commercially available monomer liquid of Palacos R was used which contains MMA with co-initiator and inhibitor in appropriate concentrations.

With cured bone cement of the afore described composition the mineralization of the cement surface was examined. For this purpose, samples were incubated while suspended, with the sample surface in vertical position, in a simple simulated body fluid (SBF). An exchange of SBF after 24 h, 48 h and 5 d was performed. As a reference sample (comparative example) a sample of a bone cement produced in the same way without addition of anionic copolymer nanoparticles, $CaCl_2$ and $Na_2CO_3$ was examined.

The mineralization of the sample surface was examined after 48 h by scanning electron microscope (SEM) (FIG. 1). The mechanical characterization was done according to ISO 5833. When comparing the two examined bone cements in the reference sample no mineral deposits are visible (FIG. 1a). In the bone cement according to the invention with HEMA-P, $Na_2CO_3$ and $CaCl_2$ (FIG. 1b) a complete coverage with mineral deposits can be seen. By means of fluorescence spectroscopic examinations these deposits were identified as calcium phosphates (hydroxyl apatite).

Moreover, the compression strength of three bone cements according to the invention (1)-(3) in comparison to a reference bone cement was tested. For this purpose, anionic copolymer nanoparticles with HEMA-P as anionic monomer were used in analogy to Example 2. The compositions of the tested bone cements (values in % by weight) can be taken from the following table.

| additive | reference | (1) | (2) | (3) |
|---|---|---|---|---|
| HEMA-P copolymer nanoparticles | 0% | 20% | 10% | 20% |
| $Na_2CO_3$ | 0% | 0% | 2.5% | 5% |
| $CaCl_2$ | 0% | 0% | 2.5% | 5% |
| bone cement powder Palacos R | 100% | 80% | 85% | 70% |
| final contents HEMA-P in bone cement | | 0.5% | 0.25% | 0.5% |

Figure 2:
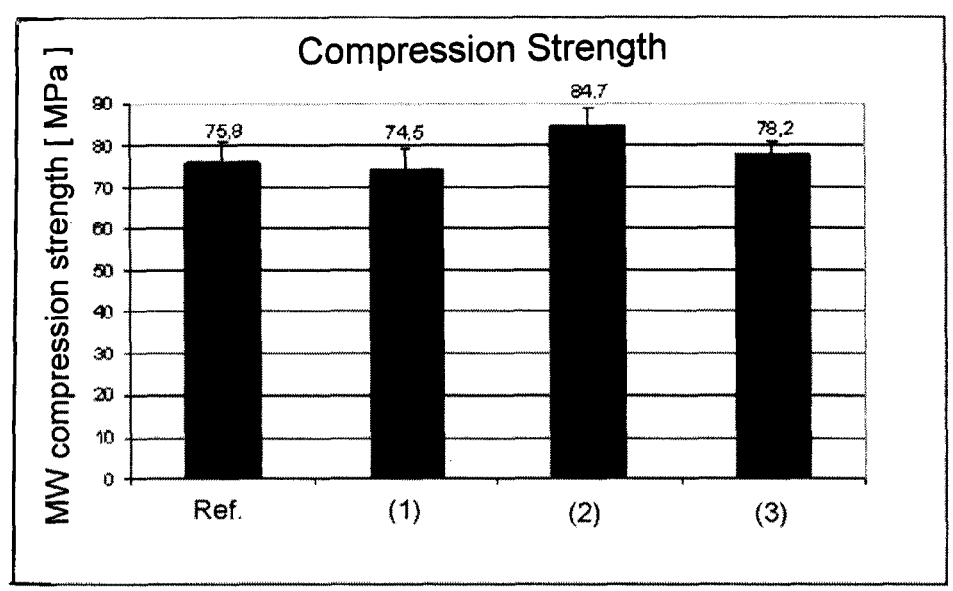
FIG. 2 compression strength of a reference bone cement (Ref) and bone cements with anionic copolymer nanoparticles, wherein in (1) exclusively anionic copolymer nanoparticles and in (2) and (3) additionally $CaCl_2$ and $Na_2CO_3$ were added.

The compression strength was tested according to ISO 5833. In FIG. 2, the compression strengths of the examined bone cements are listed. The bone cements (1)-(3) according to the invention show no worsened compression strength in comparison to the reference bone cement (here referenced as "Ref"). The bone cements according to the invention have thus mechanical properties comparable to those of conventional PMMA bone cements. They are advantageously distinguished however by mineralization of the cement surface.

Example 4

Preparation and Testing of Bioactivity of Bone Cements According to the Invention with Anionic Copolymer Nanoparticles with Methacrylic Acid (MAA) as an Anionic Co-Monomer A bone cement according to the invention has the following composition:
powder component: polymer powder (PMMA particles, Palacos R of Heraeus Medical), anionic copolymer nanoparticles with MM as anionic co-monomer (in analogy to Example 1), $CaCl_2$, $Na_2CO_3$;
reactive monomer liquid: MMA (Palacos R, with co-initiator and inhibitor).

For producing the bone cement anionic copolymer nanoparticles of Example 1 were admixed to the commercially available bone cement powder (Palacos R of Heraeus Medical). Before the mixing process the nanoparticles were ground in order to break up agglomerates. Alternatively, a nanoparticle suspension can be mixed with the bone cement powder and subsequently dried so that nano-particulate coatings of the anionic copolymer nanoparticles on the bone cement powder are obtainable.

The further additives $CaCl_2$ and $Na_2CO_3$ were first mechanically comminuted in a ball mill and subsequently admixed into the premixed nanoparticle bone cement powder. In order to ensure a homogeneous distribution of the components, the modified cement powder was mixed in a drum on a roller.

With cured bone cement of the afore described composition the mineralization of the cement surface was examined. For this purpose, the samples were incubated while suspended, with the sample surface in vertical position, in a simple SBF. An exchange of SBF after 24 h and 5 d was carried out. As a reference sample a sample of a bone cement produced in the same way without addition of anionic copolymer nanoparticles, $CaCl_2$ and $Na_2CO_3$ was examined.

The mineralization of the sample surface was examiner by scanning electron microscope. The mechanical characterization was carried out according to ISO 5833.

The following table shows the composition of the individual solid additives to the powder component of the bone cement according to the invention in % by weight (middle column) as well as the contents of the anionic monomer MAA in the cured bone cement. Compositions of bioactive cement with MAA copolymer:

| additive | proportion additive [% by weight] | final contents MAA in bone cement |
|---|---|---|
| MAA copolymer nanoparticles | 10% | 0.5% |
| $Na_2CO_3$ | 5% | |
| $CaCl_2$ | 5% | |
| bone cement powder Palacos R | 80% | |

Subsequently, the bone cement powder was mixed with monomer liquid in a ratio of 2:1 (weight of powder/volume of monomer). As a monomer MMA was used. A commercially available monomer liquid of Palacos R was used which contains MMA with co-initiator and inhibitor in appropriate concentrations.

Figure 3:
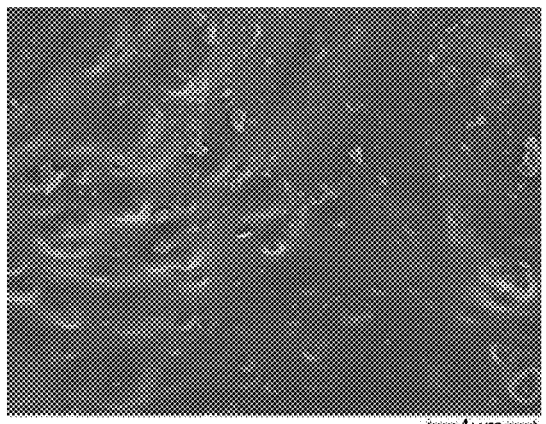
FIG. 3 REM images of cured bone cements after incubation in SBF. (a) reference bone cement (REF), (b) bone cements with anionic copolymer nanoparticles (with MAA as anionic monomer), $CaCl_2$ and $Na_2CO_3$.
Figure 3:
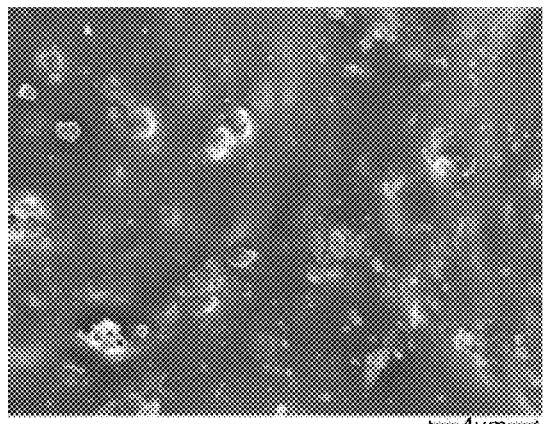
Figure 3:
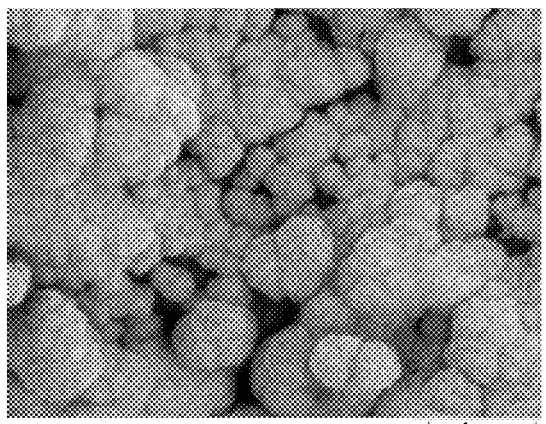
Figure 3:
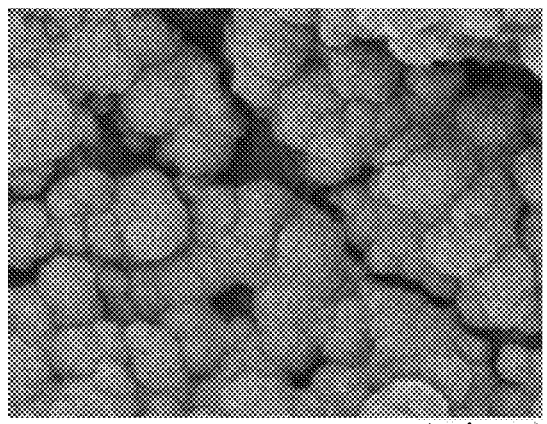

The mineralization of the sample surface was examined after 48 h and 7 d by scanning electron microscope (SEM) (FIG. 3). The mechanical characterization was carried out in accordance with ISO 5833. When comparing the two examined bone cements, in the reference sample (FIG. 3a and FIG. 3b) at both points in time no mineral deposits are visible. In the bone cement according to the invention with MM, $Na_2CO_3$ and $CaCl_2$ a coating with mineral deposits can be seen (FIGS. 3c and 3d, (MAA, $Na_2CO_3$, $CaCl_2$)) that is comparable to the mineral deposits when adding HEMA-P copolymer (FIG. 1). By means of fluorescence spectroscopic examinations these deposits were identified as calcium phosphates (hydroxyl apatite).

Example 5

Implantation of a Bone Cement According to the Invention in Rabbits

A bone cement according to the invention in analogy to Example 3 was examined in an implantation study in rabbits. The bone cement had the following composition:
powder component: 70% Palacos R, 20% HEMA-P copolymer nanoparticles, 5% $CaCl_2$, 5% $Na_2CO_3$,
reactive monomer liquid: MMA (Palacos R, with co-initiator and inhibitor).

Powder component and monomer liquid were mixed in a ratio of 2:1 (weight of powder/volume of monomer). The composition corresponds to a final contents of 0.5% HEMA-P in the cured bone cement.

As a reference a bone cement was examined whose powder component is comprised to 100% of Palacos R.

For the implantation a spacer implant in the femur was secured on two sides by bone cement or a bone cement plug in the tibia. The implanted bone cements were evaluated histologically after 3 and 7 months by determination of the bone affinity index (BAI). The BAI describes the proportion of bone cement/bone interface that is characterized by direct contact between bone and cement without connective tissue and therefore provides a parameter for the bioactivity of the bone cement.

Figure 4:
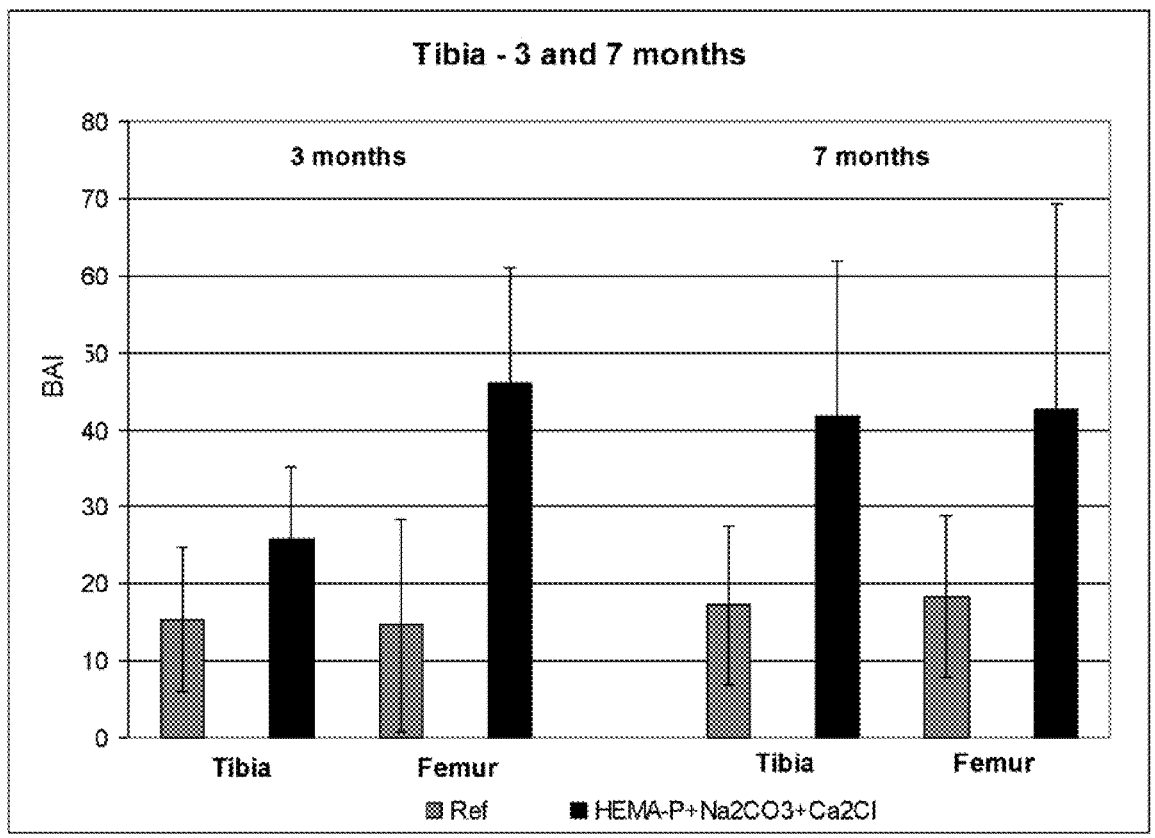
FIG. 4 comparison of bone affinity index (BAI) after implantation of bone cement in tibia and femur of rabbits. Left bar shows reference bone cement (Ref), right bar shows bone cement with anionic copolymer nanoparticles (with HEMA-P as anionic monomer), $CaCl_2$, $Na_2CO_3$.
Figure 5:
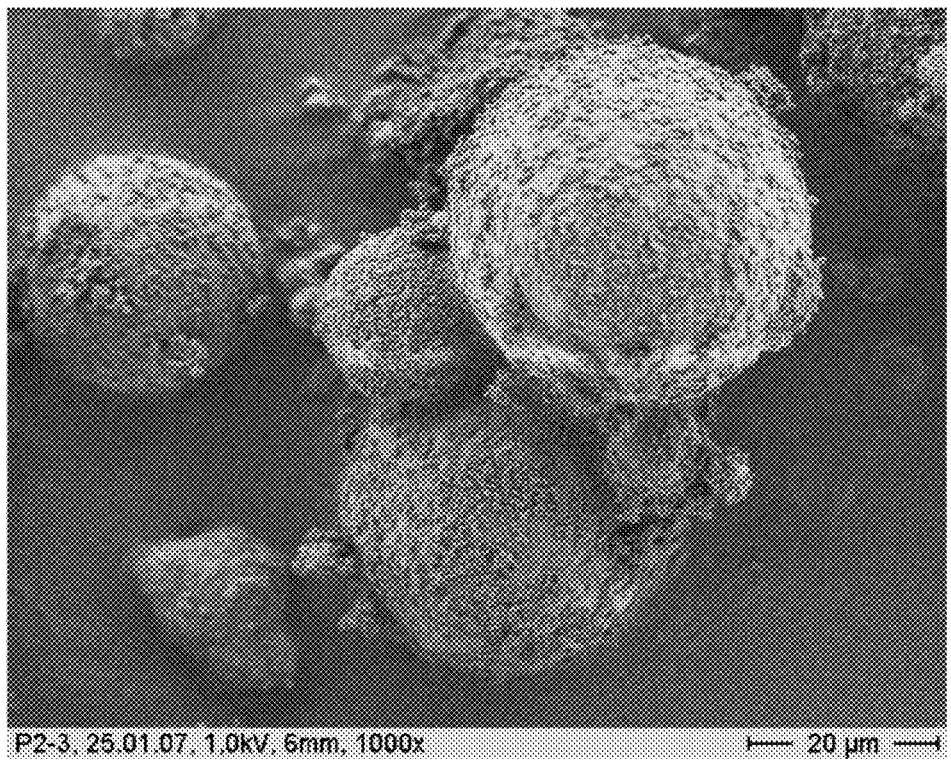
FIG. 5 REM images of powder components of bone cements with anionic copolymer nanoparticles with (a) MAA as anionic monomer and (b) HEMA-P as anionic monomer. Anionic copolymer nanoparticles are present as nano-particulate coatings on the PMMA bead polymers.
Figure 5:
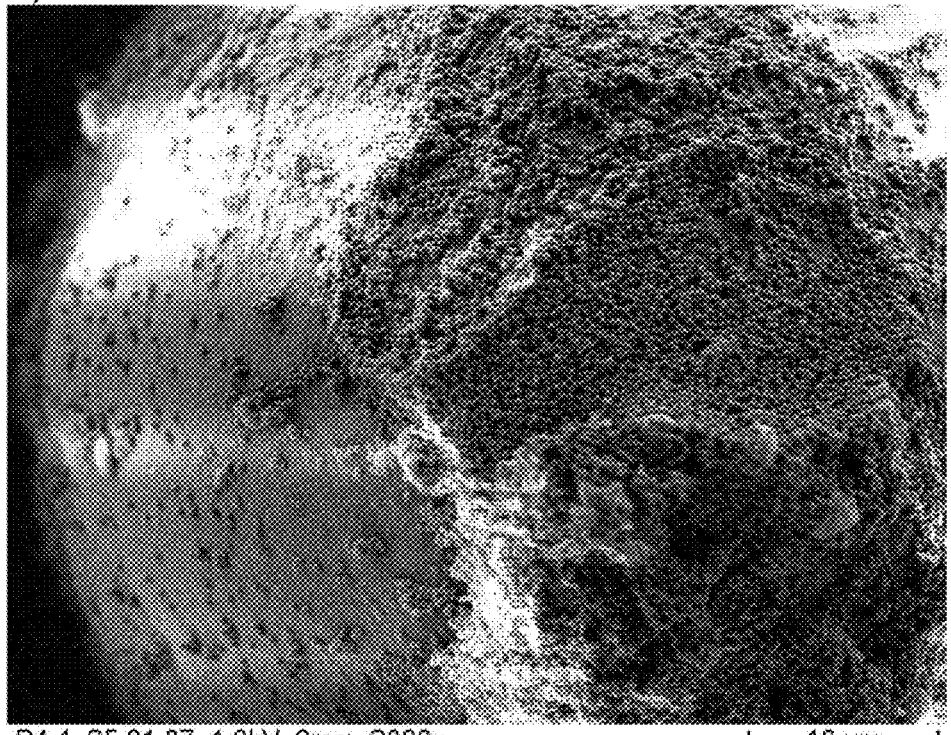

FIG. 4 shows the comparison of the BAI values for the reference bone cement and the bone cement according to the present invention 3 and 7 months after implantation. The bone cement according to the invention is characterized generally by increased bone attachment in comparison to the reference cement. The bioactivity is thus significantly increased in the bone cement according to the invention. In particular in the femur area a significant difference of the BAI value between reference cement and bone cement was observed (wherein the bone cement according to the present invention exhibits the higher BAI values). This was determined 3 months as well as 7 months after implantation.

In a further test group with the same implantation model bone cements according to the invention in analogy to the Examples 3, 8 and 10 were examined.

The bone cements according to the invention had the following composition:
powder component (+HEMA-P): 80% Palacos R, 20% HEMA-P copolymer nanoparticles
powder component (+HEMA-P, +$Na_2CO_3$): 75% Palacos R, 20% HEMA-P copolymer nanoparticles, 5% $Na_2CO_3$ powder component (+HEMA-P, +Na$_2$CO$_3$, +CaCl$_2$): 70% Palacos R, 20% HEMA-P copolymer nanoparticles, 5% CaCl$_2$, 5% Na$_2$CO$_3$ Moreover a reference bone cement as a comparative example was examined whose powder component consisted to 100% of Palacos R.

As a reactive monomer liquid in combination with the differently composed powder components the commercially available MMA liquid of Palacos R was used. Powder component and monomer liquid were mixed in a ratio of 2:1 (weight of powder/volume of monomer).

For the implantation a spacer implant in the femur was secured on two sides with bone cement. The implanted bone cements were evaluated histologically after 3 months by determination of the bone affinity index (BAI).

Figure 7:
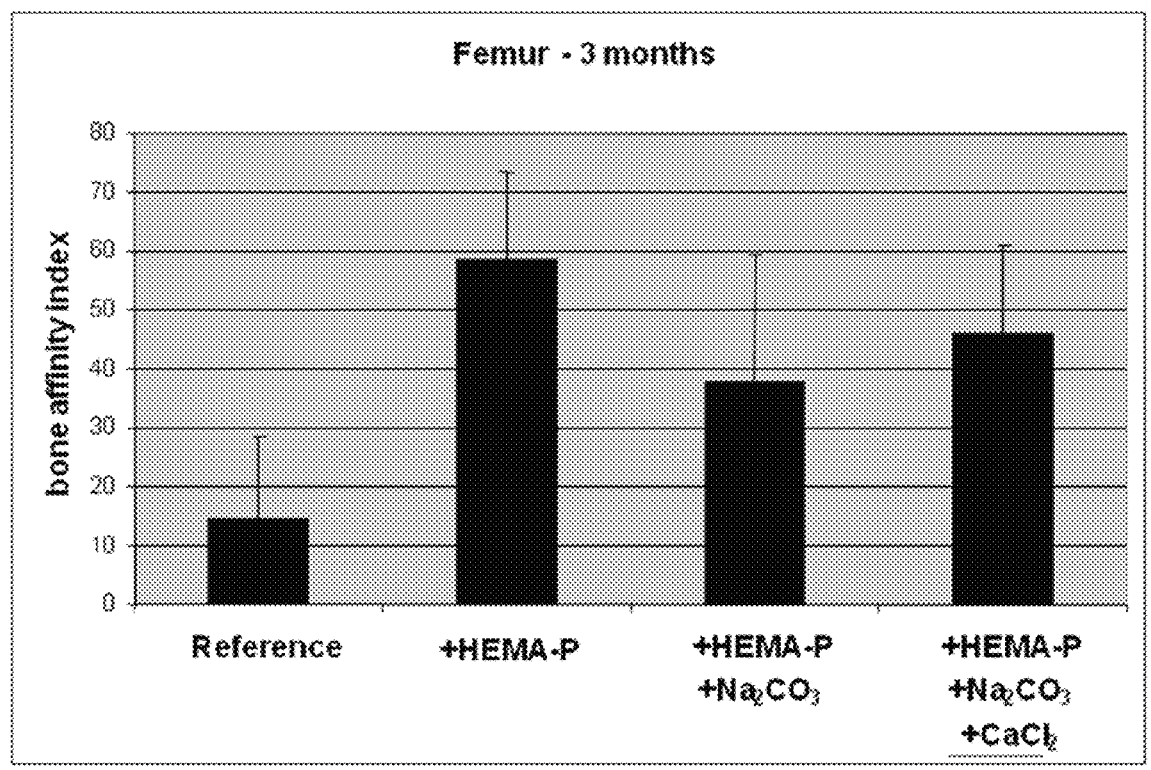
FIG. 7 comparison of bone affinity index (BAI) after implantation of bone cement in femur of rabbits. Illustrated are reference bone cement (reference, comparative example), bone cement with anionic copolymer nanoparticles with HEMA-P as anionic monomer without further additives (+HEMA-P), with addition of $Na_2CO_3$ (+HEMA-P, +$Na_2CO_3$), and with addition of $Na_2CO_3$ and $CaCl_2$ (+HEMA-P, +$Na_2CO_3$, +$CaCl_2$).

FIG. 7 shows a comparison of the BAI values for the reference bone cement and the bone cements according to the invention 3 months after implantation.

The results show that the addition of anionic copolymer nanoparticles with HEMA-P as anionic monomer alone already provides a significant increase of BAI relative to the reference. The further additives in this model cause no further increase of BAI. The differences in BAI relative to the reference and according to statistical evaluation in all 3 modifications are significant. The differences between the modified cements are not significant.

Example 6

Antibiotic Release from a Bone Cement According to the Invention

Many of the bone cements that are used in clinical practice contain antibiotics, usually gentamicin or tobramycin for avoiding foreign body-associated infections. For examination of the release of antibiotics from bone cements according to the invention first bone cement compositions with tobramycin in the following basic formulation is provided:

89% of bone cement powder
10% barium sulfate (as an x-ray contrast agent)
1% benzoyl peroxide (as a radical starter).

The cement powder containing tobramycin had added 1.0 g of the antibiotic (relative to the active substance) per 40 g cement powder.

Different compositions of bone cement powder were used wherein a reference bone cement (Ref as comparative example) and four bone cements according to the invention (1)-(4) (with HEMA-P copolymer nanoparticles in analogy to Example 2) were provided:

| additive | Ref | (1) | (2) | (3) | (4) |
|---|---|---|---|---|---|
| HEMA-p copolymer nanoparticles | 0% | 20% | 20% | 20% | 20% |
| Na$_2$CO$_3$ | 0% | 0% | 0% | 0% | 1% |
| CaCl$_2$ | 0% | 0% | 1% | 2.5% | 1% |
| bone cement powder Palacos R | 100% | 80% | 79% | 77.5% | 78% |

The components of the bone cement powder Simplex P were intensively mixed in a ball mill and provided with the additives listed in the table and subsequently mixed intensively one more time.

Subsequently, the bone cement powder was mixed with monomer liquid in a ratio of 2:1 (weight of powder/volume monomer). For this purpose, monomer liquid of MMA of Simplex P was used with the contained co-initiator and inhibitor concentrations.

Cylindrical sample bodies (9 mm diameter, 20 mm height) were prepared from the bone cement in silicone molds. They were cured for 24 h at 37° C. in the mold and subsequently incubated with 10 ml phosphate buffer pH 7.4 at 37° C.

During the release examination a dynamic loading of the sample bodies with a frequency of 1 Hz and a force of 100 N ("relieved" state) up to 1,500 N ("loaded" state) was applied.

Figure 6:
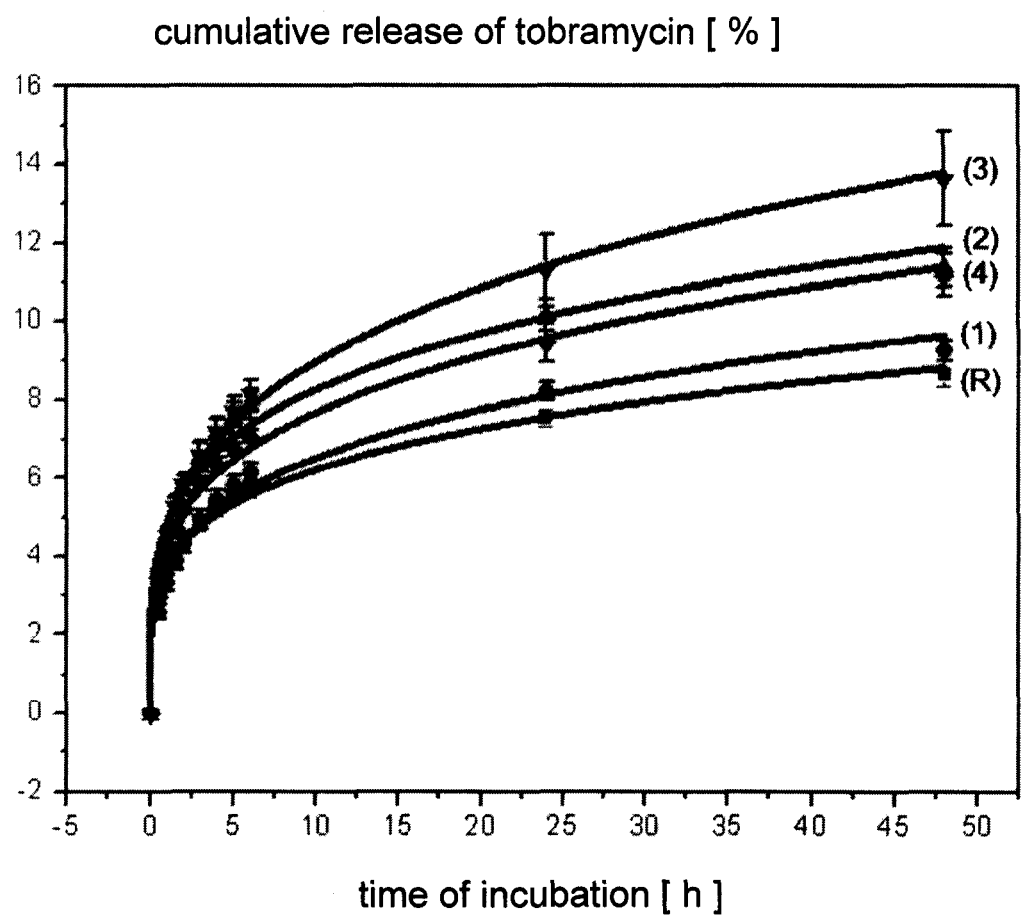
FIG. 6 release of tobramycin from reference bone cement (R) and bone cement with anionic copolymer nanoparticles (1), anionic copolymer nanoparticles and $CaCl_2$ (2, 3) as well as anionic copolymer nanoparticles, $CaCl_2$ and $Na_2CO_3$ (4).

At the points in time illustrated in FIG. 6 a sample of the phosphate buffer was photometrically examined and in this way the tobramycin concentration contained therein determined.

The release of tobramycin is illustrated in FIG. 6. The addition of anionic copolymer nanoparticles alone shows no significant effect on the release of the antibiotic (FIG. 6; compare Ref. and (1)). Active ingredients such as antibiotics are therefore released from the bone cements according to the invention in a way comparable to the release in conventional bone cements. The addition of CaCl$_2$ significantly increases the antibiotics release (bone cements (2) to (4) of the present invention).

The employed bone cements were also examined with regard to their compression strength. No significant differences to the compression strength was observed (data not shown).

Example 7

Preparation of a Bone Cement According to the Invention with Anionic Copolymer Nanoparticles with Methacrylic Acid (MAA) as Anionic Co-Monomer The bone cement according to the invention has the following composition:

powder component: polymer powder (PMMA powder, Palacos R of Heraeus Medical), anionic copolymer nanoparticles with MM as anionic co-monomer (in analogy to Example 1);

reactive monomer liquid: MMA of Palacos R with initiator and incubator concentrations contained therein.

For producing the bone cement anionic copolymer nanoparticles of Example 1 were admixed into the commercially available bone cement powder (Palacos R of Heraeus Medical). Before the mixing process the nanoparticles were ground in order to break up agglomerates. Alternatively, a nanoparticle suspension can be mixed with the bone cement powder and subsequently dried so that nanoparticulate coatings of the anionic copolymer nanoparticles on the bone cement powder are obtainable.

In order to ensure homogeneous distribution of the components, the modified cement powder was mixed in a drum on a roller.

Example 8

Preparation of a Bone Cement According to the Invention with Anionic Copolymer Nanoparticles with HEMA-P as Anionic Co-Monomer The bone cement according to the invention has the following composition:

powder component: polymer powder (PMMA powder, Palacos R of Heraeus Medical), anionic copolymer nanoparticles with HEMA-P as anionic co-monomer (in analogy to Example 2);

reactive monomer liquid: MMA of Palacos R with initiator and inhibitor concentrations contained therein.

For producing the bone cement anionic copolymer nanoparticles of Example 2 were mixed with the commercially available bone cement powder (Palacos R of Heraeus Medical). Before the mixing process the nanoparticles were ground in order to break up agglomerates. Alternatively, a nanoparticle suspension can also be mixed with the bone cement powder and subsequently dried so that nano-particulate coatings of the anionic copolymer nanoparticles on the bone cement powder are obtainable.

In order to ensure a homogeneous distribution of the components the modified cement powder was mixed in a drum on a roller.

Example 9

Preparation of a Bone Cement According to the Invention with Anionic Copolymer Nanoparticles with Methacrylic Add (MAA) as Anionic Co-Monomer The bone cement according to the invention has the following composition:
powder component: polymer powder (PMMA powder, Palacos R of Heraeus Medical), anionic copolymer nanoparticles with MAA as anionic co-monomer (analog to Example 1), $CaCl_2$;
reactive monomer liquid: MMA of Palacos R with initiator and inhibitor concentrations contained therein.

For producing the bone cement anionic copolymer nanoparticles of Example 1 were mixed into the commercially available bone cement powder (Palacos R of Heraeus Medical). Before the mixing process the nanoparticles were ground in order to break up agglomerates. Alternatively, a nanoparticle suspension can be mixed with the bone cement powder and subsequently dried so that nano-particulate coatings of the anionic copolymer nanoparticles on the bone cement powder are obtainable.

$CaCl_2$ was first mechanically comminuted in a ball mill and subsequently mixed into the premixed nanoparticle bone cement powder. In order to ensure a homogeneous distribution of the components, the modified cement powder was mixed in a drum on a roller.

Example 10

Preparation of a Bone Cement According to the Invention with Anionic Copolymer Nanoparticles with HEMA-P as Anionic Co-Monomer A bone cement according to the invention has the following composition:
powder component: polymer powder (PMMA particles, Palacos R of Heraeus Medical), anionic copolymer nano particles with HEMA-P as anionic co-monomer (in analogy to Example 2), $Na_2CO_3$,
reactive monomer liquid: MMA For producing the bone cement anionic copolymer nanoparticles of Example 1 were mixed into the commercially available bone cement powder (Palacos R of Heraeus Medical). Before the mixing process the nanoparticles were ground in order to break up agglomerates. Alternatively, a nanoparticle suspension can be mixed with the bone cement powder and subsequently dried so that nano-particulate coatings of the anionic copolymer nanoparticles on the bone cement powder are obtainable.

$Na_2CO_3$ was first mechanically comminuted in a ball mill and subsequently mixed into the premixed nanoparticle bone cement powder. In order to ensure a homogeneous distribution of the components the modified cement powder was mixed in a drum on a roller.

What is claimed is:

1. A bioactive PMMA (polymethylmethacrylate) bone cement comprising:
a powder component comprising:
particulate polymer powder of polymethylmethacrylates;
a radical starter; and
anionic copolymer nanoparticles consisting of anionic co-oligomers or of anionic copolymers, wherein the anionic co-oligomers or anionic copolymers consist of first monomer units that are selected from the group consisting of acrylate, methacrylate, styrene, vinyl monomers, and monomers with ethylenically unsaturated double bond, and of second monomer units with free anionic groups or anionic groups that dissociate or hydrolyze when in contact with an aqueous solution, the anionic groups selected from the group consisting of carboxyl, phosphate, phosphonate, and sulfate, wherein the anionic copolymer nanoparticles are distributed in nano-particulate form within the powder component or coated as a film on particles of the particulate polymer powder;
a reactive monomer liquid;
wherein when the powder component and the reactive monomer liquid are mixed with each other, the anionic copolymer nanoparticles dissolve quickly in the reactive monomer and the powder component and the reactive monomer react with one another and form a polymer-based solid material.

2. The bone cement according to claim 1, wherein the anionic copolymer nanoparticles are present as nano-particulate coatings on the particulate polymer powder.

3. The bone cement according to claim 1, wherein the anionic copolymer nanoparticles have a size of 30 nm to 5,000 nm.

4. The bone cement according to claim 1, wherein the second monomer units are present in a molar proportion of 0.01% to 25%.

5. The bone cement according to claim 1, wherein the proportion of the anionic copolymer nanoparticles in the powder component is 0.1% to 50% by weight.

6. The bone cement according to claim 1, wherein a proportion of the anionic copolymers is not crosslinked.

7. The bone cement according to claim 1, wherein the powder component further comprises non-anionic copolymer nanoparticles.

8. The bone cement according to claim 1, further comprising a carrier liquid, wherein the powder component is combined with the carrier liquid to a storage-stable paste.

9. The bone cement according to claim 1, wherein the powder component further comprises at least one additive selected from the group consisting of water-soluble calcium salts, biocompatible buffering substances, x-ray contrast agents, antibiotics, antimicrobial agents, and anti-inflammatory agents.

10. The bone cement according to claim 1, formulated in a mixing system wherein the powder component and the reactive monomer liquid are contained in spatially separate containers.

11. The bone cement according to claim 10, wherein the mixing system is a ready-made system in sterilized form.

12. The bone cement according to claim 1 in the form of a kit comprised of two or more separately packaged components containing the powder component and the reactive monomer liquid, respectively, wherein the packaged components are matched to one another in regard to quantity ratios and are combined with one another not until immediately before use.

13. The bone cement according to claim 1 as an anchoring cement for prosthesis components in the bone, as a cement for reinforcing bone, as a cement for filling and reconstructing bone defects of all kinds, as a dowel for bone screws, and as implant material for anchoring screws and other implants for osteosynthesis.

14. The bone cement according to claim 1, wherein the powder component further comprises at least one additive for increasing mineralization, the at least one additive selected from the group consisting of water-soluble calcium salts and biocompatible buffering substances.

* * * * *